US008343644B2

(12) United States Patent
Vaisnys et al.

(10) Patent No.: US 8,343,644 B2
(45) Date of Patent: Jan. 1, 2013

(54) MEDICAL DEVICE WITH A MULTIPLE FUNCTION BATTERY STATUS INDICATOR

(75) Inventors: Gintaras A. Vaisnys, Chicago, IL (US); Giovanni C. Meier, Madison, CT (US); Glenn W. Laub, Princeton, NJ (US)

(73) Assignee: Defibtech, LLC, Guilford, CT (US)

( * ) Notice: Subject to any disclaimer, the term of this patent is extended or adjusted under 35 U.S.C. 154(b) by 113 days.

(21) Appl. No.: 12/960,788

(22) Filed: Dec. 6, 2010

(65) Prior Publication Data

US 2011/0137361 A1  Jun. 9, 2011

Related U.S. Application Data

(60) Continuation of application No. 12/624,873, filed on Nov. 24, 2009, now Pat. No. 7,855,010, which is a continuation of application No. 11/185,476, filed on Jul. 20, 2005, now Pat. No. 7,625,662, which is a division of application No. 09/960,204, filed on Sep. 21, 2001, now Pat. No. 6,955,864.

(51) Int. Cl.
*H01M 10/48* (2006.01)
*H01M 2/10* (2006.01)

(52) U.S. Cl. ................. 429/90; 429/92; 429/93; 429/96; 607/5

(58) Field of Classification Search .................. 429/50, 429/90, 92, 93, 7, 149, 9, 61, 96, 100; 607/27, 607/29, 5; 320/136, 165; 340/636.1, 636.19; 362/9, 194
See application file for complete search history.

(56) References Cited

U.S. PATENT DOCUMENTS

| 4,590,943 | A | 5/1986 | Paull et al. |
|---|---|---|---|
| 5,224,870 | A | 7/1993 | Weaver et al. |
| 5,350,317 | A | 9/1994 | Weaver et al. |
| 5,372,605 | A | 12/1994 | Adams et al. |
| 5,470,343 | A | 11/1995 | Fincke et al. |
| 5,483,165 | A | 1/1996 | Cameron et al. |
| 5,579,234 | A | 11/1996 | Wiley et al. |
| 5,591,213 | A | 1/1997 | Morgan |
| 5,640,078 | A | 6/1997 | Kou et al. |
| 5,645,571 | A | 7/1997 | Olson et al. |
| 5,697,322 | A | 12/1997 | Hay et al. |
| 5,697,955 | A | 12/1997 | Stolte |
| 5,700,281 | A | 12/1997 | Brewer et al. |
| 5,721,482 | A | 2/1998 | Benvegar et al. |
| 5,741,305 | A | 4/1998 | Vincent et al. |
| 5,749,902 | A | 5/1998 | Olson et al. |
| 5,773,961 | A | 6/1998 | Cameron et al. |
| 5,792,190 | A | 8/1998 | Olson et al. |
| 5,797,969 | A | 8/1998 | Olson et al. |
| 5,800,460 | A | 9/1998 | Powers et al. |
| 5,817,151 | A | 10/1998 | Olson et al. |
| D405,754 | S | 2/1999 | Barkley et al. |

(Continued)

OTHER PUBLICATIONS

Heartstream®, Fore Runner® Semi-Automatic Defibrillator User's Guide, pp. 6-9 and 50, (assumed published prior to filing date).

(Continued)

*Primary Examiner* — Raymond Alejandro
(74) *Attorney, Agent, or Firm* — King & Spalding LLP

(57) ABSTRACT

A medical device having a battery pack comprising an indicator, wherein the battery pack indicator indicates the status of the battery pack when the battery pack is disassociated from the medical device and indicates the status of the medical device when associated with the medical device.

4 Claims, 5 Drawing Sheets

U.S. PATENT DOCUMENTS

| | | | |
|---|---|---|---|
| 5,868,790 | A | 2/1999 | Vincent et al. |
| 5,868,794 | A | 2/1999 | Barkley et al. |
| 5,879,374 | A | 3/1999 | Powers et al. |
| 5,889,388 | A | 3/1999 | Cameron et al. |
| 5,897,576 | A | 4/1999 | Olson et al. |
| D409,752 | S | 5/1999 | Bishay et al. |
| 5,904,707 | A | 5/1999 | Ochs et al. |
| 5,919,212 | A | 7/1999 | Olson et al. |
| 5,944,741 | A | 8/1999 | Ochs et al. |
| 5,955,956 | A | 9/1999 | Stendahl et al. |
| 5,964,786 | A | 10/1999 | Ochs et al. |
| 5,983,137 | A | 11/1999 | Yerkovich |
| 5,999,493 | A | 12/1999 | Olson |
| 6,016,059 | A | 1/2000 | Morgan |
| 6,021,352 | A | 2/2000 | Christopherson et al. |
| 6,038,473 | A | 3/2000 | Olson |
| 6,072,299 | A | 6/2000 | Kurle et al. |
| 6,304,779 | B1 * | 10/2001 | Yerkovich .......................... 607/5 |
| 6,366,809 | B1 | 4/2002 | Olson et al. |
| 6,577,102 | B1 | 6/2003 | Vaisnys et al. |
| 6,650,942 | B2 | 11/2003 | Howard et al. |
| 7,495,413 | B2 | 2/2009 | Vaisnys et al. |
| 2010/0075208 | A1 | 3/2010 | Vaisnys et al. |

OTHER PUBLICATIONS

Hewlett Packard, 43110 A Defibrillator/Monitor Operating Guide, Eighth Edition, pp. 2, 5, 36-39 Aug. 1991.

Aligent Heartstream FR2, M3860A, M3861A, User's Guide, pp. 2-1-2-2,204, 4-5, and B6 (assumed published prior to filing date).

Medtronic Physio-Control, Lifepack® 500 automated external defibrillator, Service Manual pp. 3 of 12-4-12, 7 of 12-10 of 12, 12 of 12, (assumed published prior to filing date).

Medtronic Physio-Control, Lifepak® 500 Automated External Defibrillator Operating Instructions, pp. 2-5, 2-6, 5-7-5-11, 5-16-5-17, Mar. 2001.

Survivalink First5ave™ Operation and Service Manual, pp. 20, 29-31, 65, 70, 84 and 85, 2000.

* cited by examiner

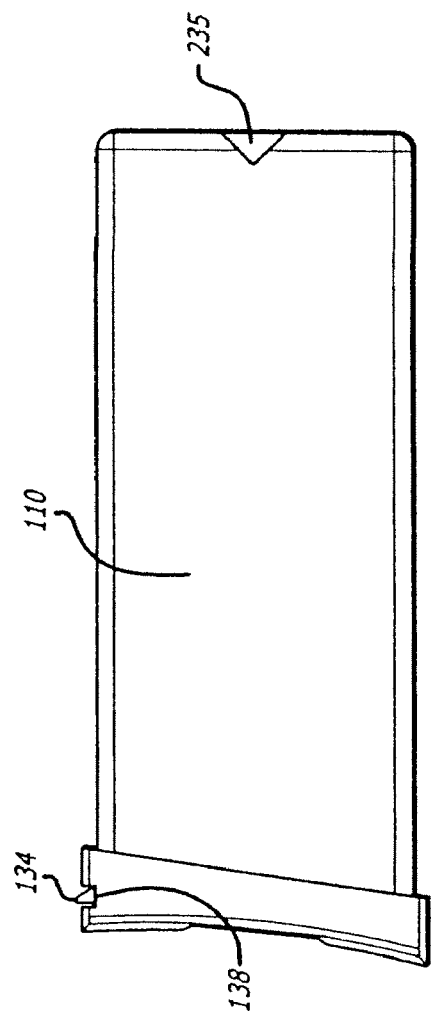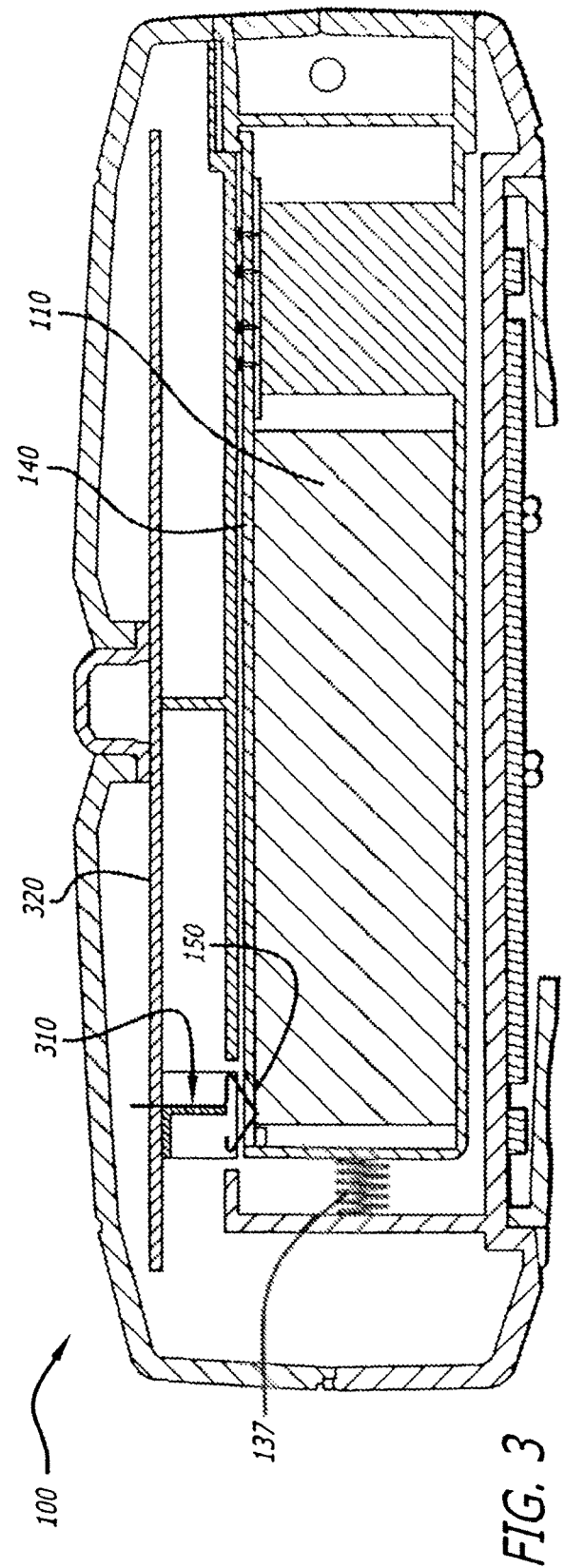

MEDICAL DEVICE WITH A MULTIPLE FUNCTION BATTERY STATUS INDICATOR

CROSS-REFERENCE TO RELATED APPLICATIONS

This application is a continuation of U.S. patent application Ser. No. 12/624,873 entitled "Medical Device Battery Pack," filed Nov. 24, 2009 (now U.S. Pat. No. 7,855,010) which is a continuation of U.S. patent application Ser. No. 11/185,476 entitled "Medical Device Battery Pack System and Method for Providing Active Status Indication," filed Jul. 20, 2005 (now U.S. Pat. No. 7,625,662), which is a divisional of U.S. patent application Ser. No. 09/960,204 entitled "Medical Device Battery Pack with Active Status Indication," filed Sep. 21, 2001 (now U.S. Pat. No. 6,955,864). The complete disclosure of each of the above-identified applications is hereby fully incorporated herein by reference.

FIELD OF THE INVENTION

The present invention relates generally to battery packs, and more specifically relates to battery packs for a medical device, where the battery pack includes an active status indicator.

BACKGROUND

Many known battery-powered medical devices, such as semi-automatic external defibrillator ("AED") devices, rely on batteries to power electronics of the device, and, in the case of the AED device, to administer electric shocks to patients. For example, AED devices are used to provide electric shocks to treat patients for a variety of heart arrhythmias. The AED provides relatively high-level shocks to a patient, usually through electrodes attached to the patient's torso, to convert, for example, ventricular fibrillation to a normal sinus rhythm.

Studies have demonstrated that survival rates are high when defibrillation treatment is administered within the first few minutes following cardiac arrest. The likelihood of successful resuscitation, however, decreases by approximately 10 percent with each minute following sudden cardiac arrest. After ten minutes, very few resuscitation attempts are successful. Thus, it is advantageous to construct a portable AED to provide an operator with a better chance of responding to a patient in a timely fashion. The portable AED typically includes a portable power supply, such as a battery pack.

For a defibrillation pulse to be effective in terminating cardiac arrhythmia sufficient energy should reach the heart, through muscle, bone, organs and other tissues. To be effective, the battery pack should be able to deliver a high dose of energy when needed. Since batteries can lose energy over time, however, some battery packs include an expiration date to help an AED operator determine that the battery pack can deliver the necessary energy needed. The operator cannot tell many things from the expiration date, however, for example, whether the battery pack was previously used or whether the batteries of the battery pack contain sufficient energy to function properly. In other devices, the operator does not know the status of the battery pack until it is inserted into the medical device.

Thus, there is a need for an improved battery pack for a medical device such as an AED.

BRIEF DESCRIPTION OF THE DRAWINGS

FIG. 2 illustrates a bottom view of the battery pack.

FIG. 3 illustrates a side sectional view of the AED including the battery pack.

DETAILED DESCRIPTION

Figure 1A:
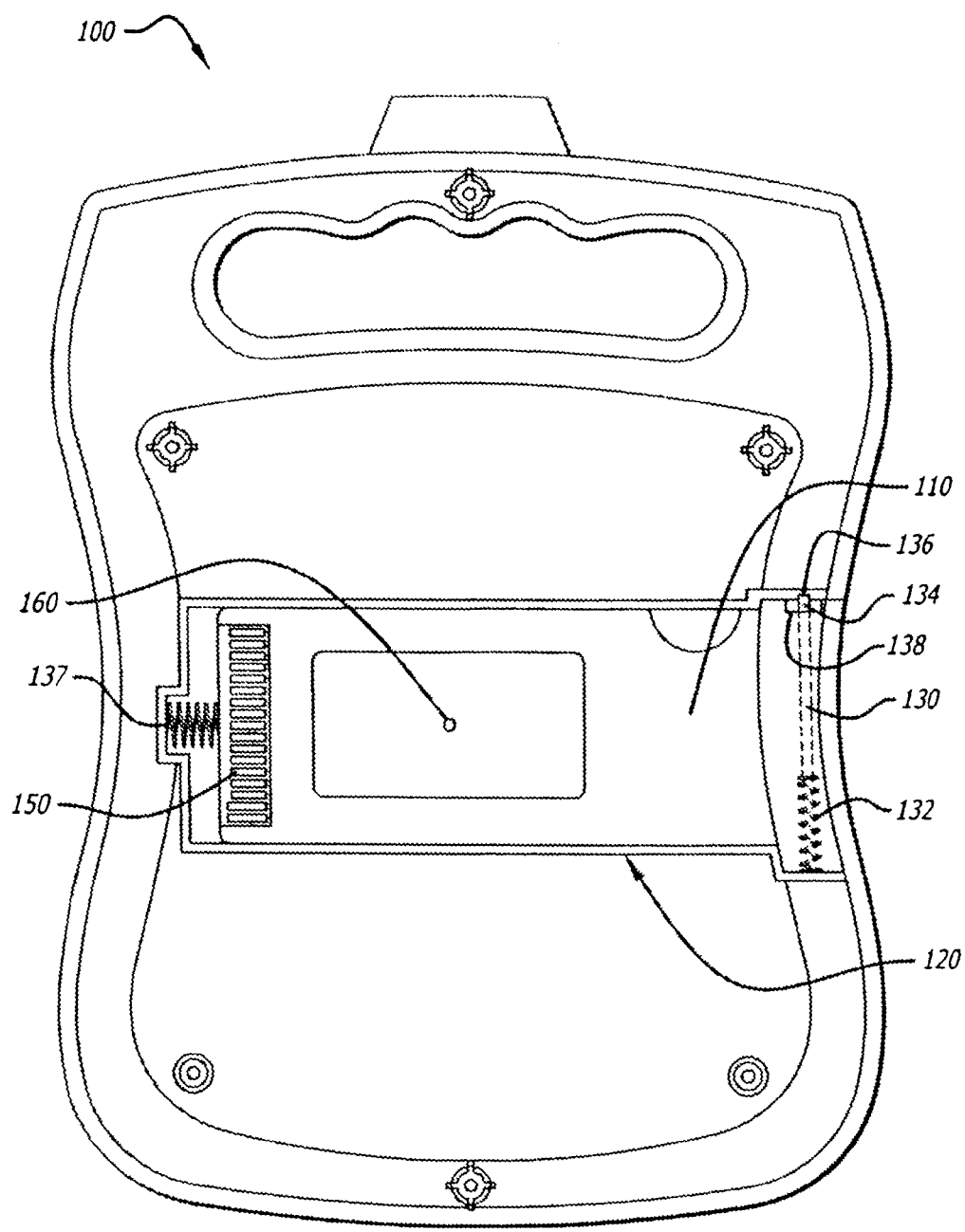
FIG. 1A illustrates a top sectional view of an AED with a battery pack installed.

FIG. 1A illustrates a top sectional view of the Semi-Automatic External Defibrillator ("AED") 100 that includes a battery system, for example battery pack 110. The AED 100 is a device to treat cardiac arrest that is capable of recognizing the presence or absence of ventricular fibrillation or rapid ventricular tachycardia or other shockable cardiac arrhythmias, and is capable of determining, without intervention by an operator, whether defibrillation should be performed. Upon determining that defibrillation should be performed, the AED automatically charges and requests delivery of electrical energy to electrodes that attach to a patient to deliver the energy to the patient's heart.

The battery pack 110 provides power to components such as electronics and a charger located in the AED 100. The charger charges a capacitor 564 (FIG. 5) of the AED 100 that provides the electrical energy to the electrodes attached to the patient. The AED 100 includes a generally rectangular shaped battery well 120 that is constructed and arranged to house the battery pack 110. The battery pack 110 is sized to slide in and out of the battery well 120 to releasably connect a power supply of the battery pack 110 to the AED 100.

Figure 1B:
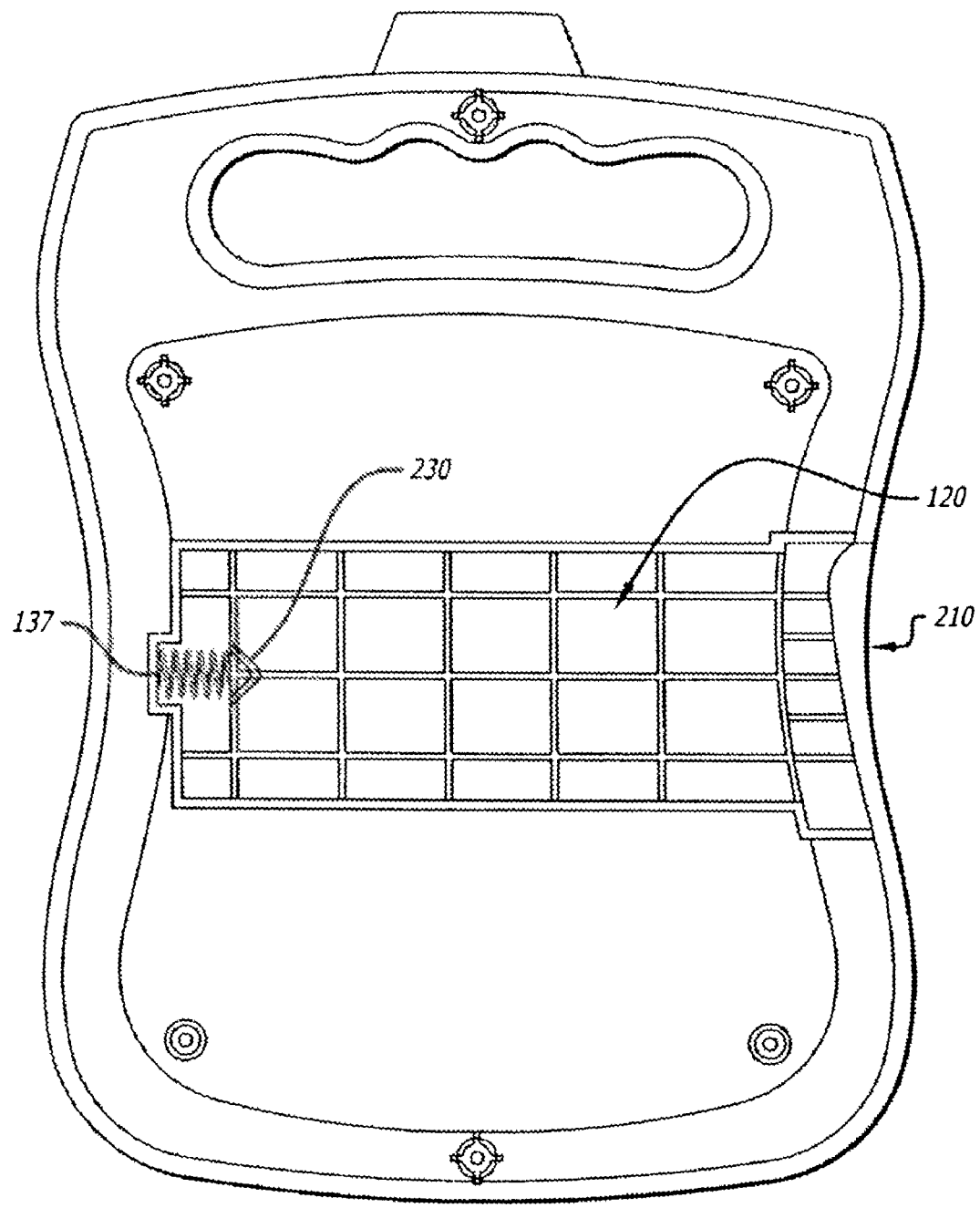
FIG. 1B illustrates a top sectional view of the AED with the battery pack removed.

FIG. 1B illustrates a top sectional view of the AED 100 and the battery well 120 with the battery pack 110 removed. An entrance 210 of the battery well 120 accommodates alignment of the battery pack 110 within the battery well 120.

FIG. 2 illustrates a bottom view of the battery pack 110. Referring to FIGS. 1B and 2, an opposite end of the battery well 120 includes a wedge-shaped feature 230 that corresponds to a wedge-shaped receptacle 235 located in the battery pack 110. When inserting the removable battery pack 110 to the AED 100, the battery pack 110 is guided along by the battery well 120 to the wedge-shaped feature 230. The battery pack 110 is aligned at the end of its travel by the wedge shaped feature 230 in the battery well 120 via the corresponding wedge shaped receptacle 235 in the battery pack 110.

Referring to FIG. 1A, to maintain the battery pack 110 in a connected position relative to the AED 100, the battery pack 110 includes a latch 130 that retains the battery pack 110 within the battery well 120 when the battery pack is fully inserted into the battery well 120. An end of the latch 130 connects with a spring 132 to bias the latch in a normally extended position. In the normally extended position, a latching end 134 of the latch 130 extends to enter a corresponding slot 136 located in the AED 100. The latch 130 is moveable in a plane parallel to the spring 132 to compress the spring 132 to release the latching end 134 from the slot 136. When the latching end 134 is released from the slot 136, an ejection spring 137 located on the AED 100 pushes on the battery pack 110 to eject the battery pack 110 from the battery well 120. The battery pack 110 includes a slot 138 from which the latch 130 extends. Even in a fully contracted position, the latch 130 extends past the slot 138.

The battery pack 110 also includes a printed circuit board (PCB) 140 including exposed electrical terminals 150 to connect the printed circuit board 140 to electrical circuitry contained in the AED 100, as described in more detail below.

Figure 5:
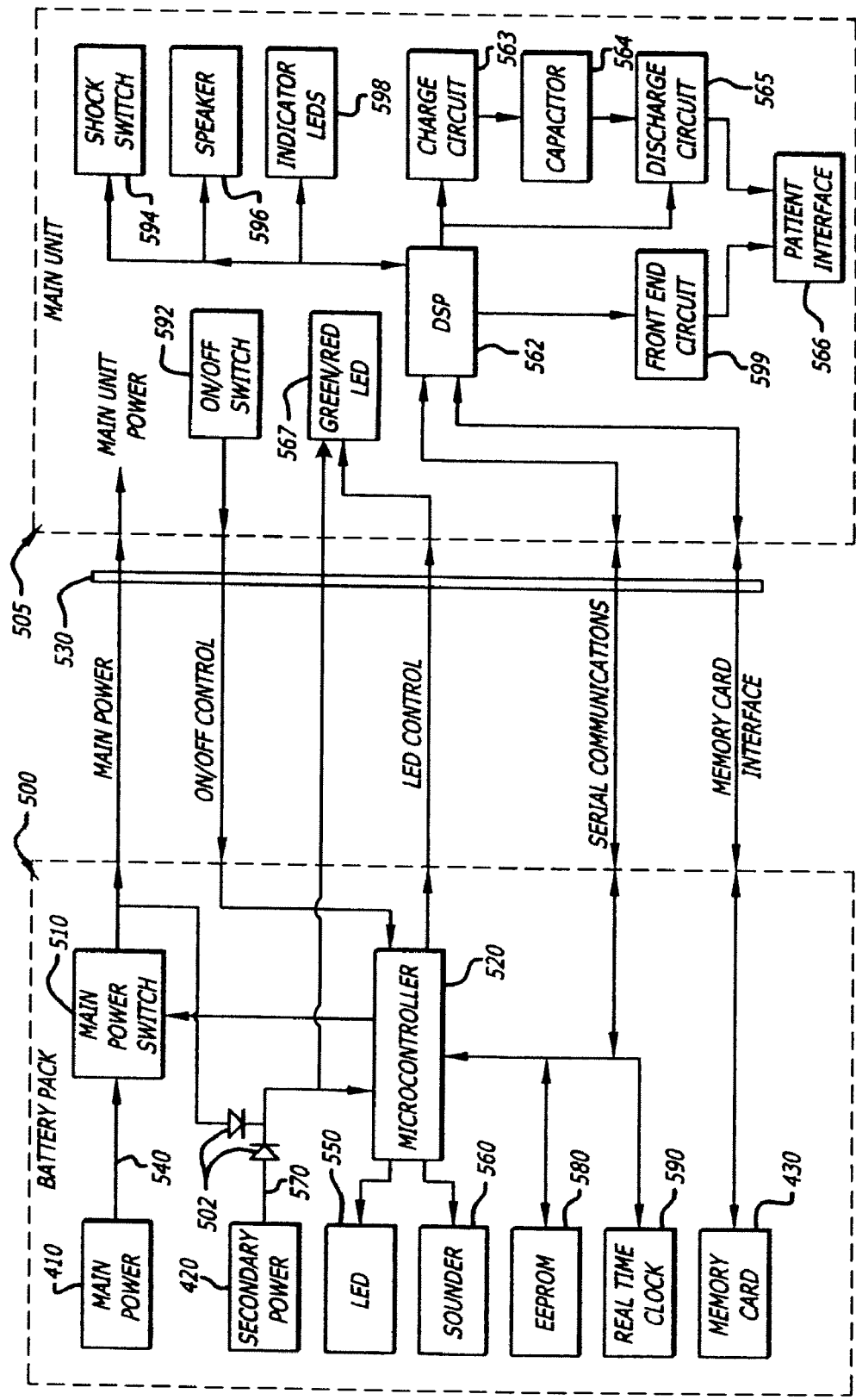
FIG. 5 illustrates a block diagram of circuitry contained with the battery pack and AED.

The PCB 140 includes electrical components that connect to circuitry of the AED 100 when the battery pack 110 is installed in the AED 100. The battery pack 110 includes a window 160 that is located proximate to a visual indicator, such as light emitting diode (LED) 550 (FIG. 5). The window 160 allows an operator to view the LED 550 when the battery pack 110 is removed from the AED 100. Thus, the operator can determine a status of at least one of the AED 100 and the battery pack 110 independent of the battery pack 110 being connected to the AED 100. It should be appreciated that the AED 100 could also include a window located proximate to the battery pack window 160 so that an operator can view the LED 550 when the battery pack is inserted in the AED 100.

FIG. 3 illustrates a side sectional view of the AED 100 including the battery pack 110. The electrical terminals 150 of the PCB 140 contact a connector 310 located within the AED 100, to electrically connect the battery pack PCB 140 with an AED PCB 320.

Figure 4:
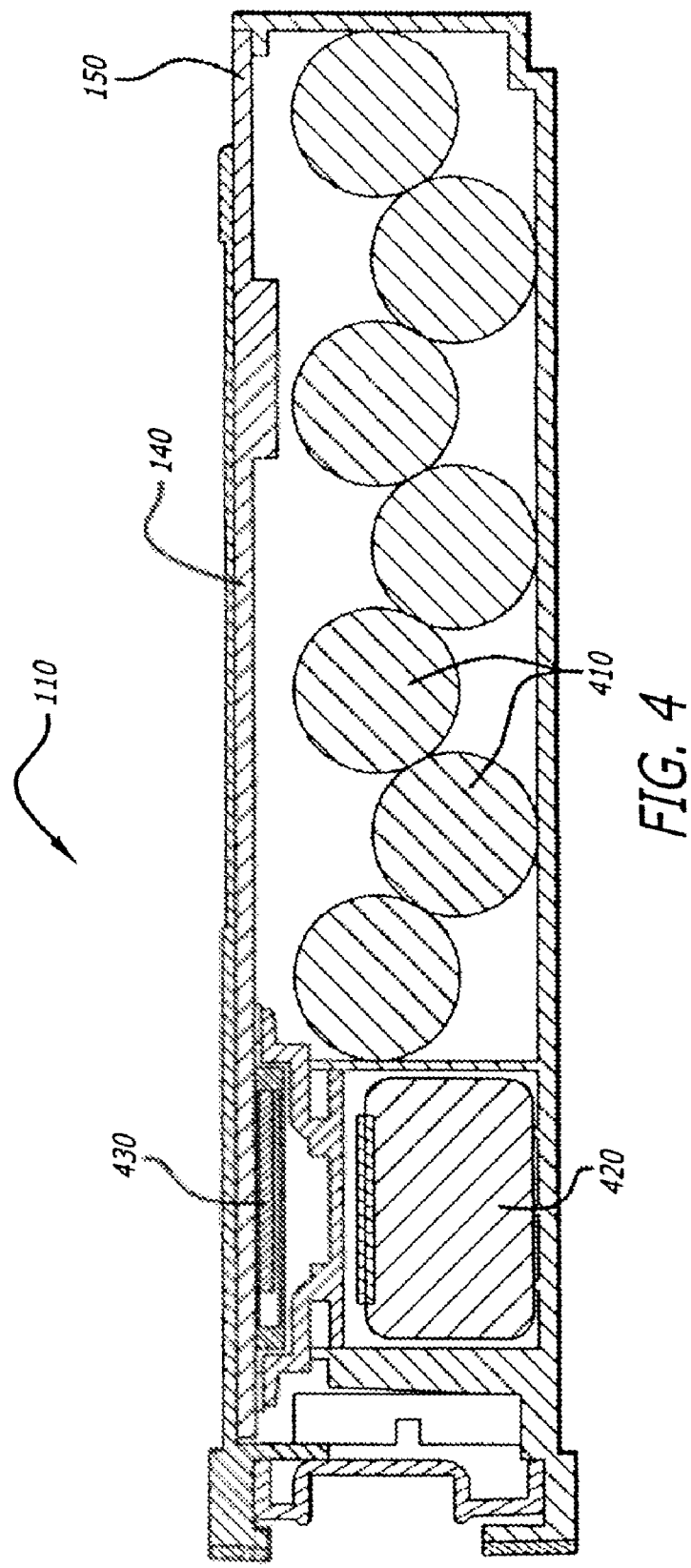
FIG. 4 illustrates a side sectional view of the battery pack including first and second battery units.

FIG. 4 illustrates a side sectional view of the battery pack 110. The battery pack 110 includes a first power supply, such as battery unit 410. The battery unit 410 powers essential power needs of the AED during a main operating mode, for example when the AED is powered on. An essential power need includes, for example, the power necessary to charge the capacitor 564 to delivery energy to the patient. The battery unit 410 is preferably not being drained of power when the AED is powered off.

The battery unit 410 includes one or more battery cells, or other power supplies, that are electrically connected together. The power supply may include other forms of energy storage, for example based on chemical or kinetic principles, such as a flywheel storage device. The battery cells can include, for example, 2/3 A size batteries and/or C size batteries. The number of batteries used varies depending on a particular application but typically includes five or ten 2/3 A size batteries or four C size batteries. The five 2/3 A size batteries or four C size batteries are connected in series. Also, two sets connected in parallel of five 2/3 A batteries connected in series can be used for the battery unit 410. The battery unit 410 preferably powers electronics and a charger located in the AED 100.

The battery pack 110 also includes a secondary power supply, such as secondary battery 420. The secondary battery 420 powers at least a portion of at least one of the AED and the battery pack 110 in an alternate mode, such as when at least a portion of the AED is powered off. Those skilled in the art will appreciate that the secondary battery 420 could also be used to power the AED during other modes, such as a sleep mode or when the AED is powered on. The secondary battery 420 typically includes a single 9 Volt battery, but other power supplies could be used, such as other sized batteries or other forms of energy storage. In a preferred embodiment, the battery pack 110 accommodates replacement of the secondary battery 420. The secondary battery 420 can be sized smaller than the battery unit 410 and contain energy sufficient to power, for example, electric circuitry of the AED 100 and the battery PCB 140.

The secondary battery 420 can be used to power circuitry exclusive of a state of the battery unit 410 and without draining power from the battery unit. Diodes 502 (FIG. 5) electrically isolate the battery unit 410 from the secondary battery 420. Electric circuitry of the battery pack PCB 140 is described in more detail below with regard to FIG. 5. Such circuitry includes a socket to removably receive a memory device (FIG. 4), such as a memory card 430 or a multi-media card (MMC).

When the AED 100 is powered on and attached to the patient, the memory card 430 records the patient's electrocardiogram (ECG) signals, audio signals received from a microphone located on the AED 100, and other operational information such as results of an analysis done on the patient by software of the AED 100. The memory card 430 may also hold files that may be used to upgrade the software of the AED 100 or to provide user training mode software for the AED.

FIG. 5 shows a block diagram illustrating battery pack circuitry 500 contained with the battery pack 110, for example, on the battery pack PCB 140, and main unit circuitry 505. The circuitry 500 includes a main power switch 510. The main power switch 510 connects with a digital logic, such as micro-controller 520, that turns the main power switch 510 on and off and controls other circuitry 500 of the battery pack PCB 140. In addition to or in place of the micro-controller 520, the digital logic can also include a microprocessor, a programmable logic device (PLD), a gate array and a custom integrated circuit. Other digital logic could also be used such as a Programmable Interface Controller (PIC) manufactured by Microchip Technologies, located in Chandler, Ariz.

The micro-controller 520 connects with a main AED connector 530 that connects circuitry of the battery pack PCB 140 to circuitry of the AED 100. When the operator engages a power switch 592 located on the AED 100, the micro-controller 520 receives a signal from the main unit connector 530 indicating that the power switch has been engaged. Thereafter, the micro-controller 520 enables the main power switch 510 to provide an electrical power between the battery unit 410 of battery pack 110 and the electronics of the AED 100. The battery pack PCB 140 also includes a main battery connector 540 to connect the battery unit 410 to the main unit connector 530 and other circuitry of the battery pack PCB 140.

The micro-controller 520 also controls a visual indicator, such as LED 550 and an audio indicator, such as sounder 560 that are used to automatically communicate information to the operator. For example, when the AED 100 fails a self-test, the operator is notified by a chirping sound from the sounder 560. Moreover, the LED 550 flashes green to indicate that a status of components of the AED 100 is within an acceptable operating range. Those skilled in the art can appreciate the opposite could be true, i.e., that a flashing light indicates a fault condition. According to a preferred embodiment, if the LED 550 is not flashing an error exists, for example, in the circuitry 500, or the battery unit 410 or secondary battery 420 are depleted. The micro-controller 520 monitors a signal of a comparator connected to secondary battery 420 to monitor a status of the secondary battery 420, for example, to determine whether or not power of the secondary battery 420 is low or depleted.

Regarding the main unit circuitry 505, a digital signal processor (DSP) 562 processes instructions and data of the AED 100. The DSP 562 connects with a charger circuit 563 and discharger circuit 565 to control the charging and discharging of main unit capacitor 564. The capacitor charger 563 connects the battery unit 410 to the capacitor 564. The capacitor 564 connects to a discharge circuit 565 that connects to patient interface 566 to deliver shocks to the patient.

The micro-controller 520 also controls a red and green LED 567, or a red LED and a green LED, located on the AED 100. The micro-controller 520 connects to the red and green LED 567, for example, via pins of the main unit connector 530. The micro-controller 520 causes the LED 567 to flash green when the AED 100 is operating properly and causes the LED 567 to flash red when components of the AED are not within the acceptable operating range, for example, a component of the AED 100 failed during a self-test procedure. If the LED 567 is not flashing when the battery pack 110 is installed into the AED 100, components of the AED 100 and the battery pack 110 should be checked. The battery pack LED 550 is preferably disabled when the battery pack 110 is installed.

The secondary battery 420 powers the micro-controller 520, the LED 550 and the LED 567, which helps to maintain the integrity of the battery unit 410 that provides power to electronics and the capacitor charger located in the AED 100. A secondary battery connector 570 connects the secondary battery 420 to the circuitry of the battery pack PCB 140.

Continuing with FIG. 5, the two diodes 502 connected and oriented as illustrated, define an OR gate between the main power 410 and the secondary power 420. An OR gate as used herein means a circuit configuration having two inputs and one output wherein the circuit elements make the inputs independent. The illustrative OR gate uses diodes 502 having the necessary orientation one to the other to make the inputs independent, such that one input is not affected by the other. Additionally, a switch 510 is located in series with the main power 410 before the OR gate. As stated above, the main power 410 has a voltage greater than the voltage of the secondary power 420. As a result, the OR gate controls which power source, main power 410 or secondary power 420, is powering the circuitry 500 in the battery pack 110. More precisely, when the main power switch 510 is open, no power flows from the main power 410 to the circuitry 500. Thus, the circuitry is powered by the secondary power 420 as the diode of the OR gate in series with the secondary power has an orientation that permits the power to flow. However, when the main power switch 510 is closed, power flows from the main power 410 into the OR gate. As the voltage of the main power 410 exceeds that of the secondary power 420, the diode connected in series with the secondary power acts as a switch effectively "turning off" the flow of power from the secondary power. As those skilled in the art will appreciate, over time the main power 410 and the secondary power 420, which are batteries, will be depleted differently. As a result, the power source having a "higher" voltage at any given time may change. The OR gate will still function as described; however, if the secondary power 420 has a higher voltage than the main power 410, the main power 410, when the switch 510 is closed, will be blocked from powering the circuitry 500, due to the diode in series with the main power 410.

The battery pack circuitry 500 also includes an electrically erasable programmable read only memory (EEPROM) 580 connected to the micro-controller 520 and the main unit connector 530. The EEPROM 580 stores information that may be relevant to an owner, service person or operator of the AED 100. The EEPROM 580 stores information regarding, for example, the number of shocks the battery unit 410 has been used for, that the AED 100 has been activated, the date of manufacture of the battery pack 110 and status information regarding a status of components of the battery pack 110 and the AED 100. The DSP 562 of the AED 100 connects to a bus that connects to a real time clock (RTC) 590, the EEPROM 580 and the micro-controller 520. Typically once per power up of the AED 100, the DSP accesses the RTC 590 to set a main unit clock of the AED 100 that is located in the DSP.

The main unit circuitry 505 also includes a switch 592, such as an ON/OFF switch, that connects to the micro-controller 520 via the main unit connector 530. A shock switch 594 connects to the DSP 562 to allow an operator to administer a shock to the patient. A speaker 596 and indicator LEDs 598 connect to the DSP 562 to supply instructions or other information to the operator. Front end circuitry 599 connects between the DSP 562 and the patient interface 566 to process and/or provide the DSP 562 with information from the patient.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

We claim:

1. An automated external defibrillator, comprising:
    a removable battery pack comprising an indicator, wherein the indicator comprises a visual output or an audible output; and
    defibrillation circuitry powered by the removable battery pack, the defibrillation circuitry in conjunction with programming running thereon configured to deliver a therapeutic shock,
    wherein the indicator comprises the dual capability of indicating a status of the removable battery pack when the removable battery pack is not connected to the defibrillation circuitry and indicating a status of the defibrillation circuitry and the removable battery pack when the battery pack is connected to the defibrillation circuitry, and wherein the automated external defibrillator comprises a battery well constructed and arranged to house the removable battery pack.

2. The automated external defibrillator of claim 1, wherein the visual output is a light.

3. An automated external defibrillator, comprising:
    a removable battery pack comprising an indicator, wherein the indicator comprises a visual output or an audible output,
    defibrillation circuitry powered by the removable battery pack and comprising an indicator, the defibrillation circuitry in conjunction with programming running thereon configured to deliver a therapeutic shock,
    wherein the removable battery pack indicator indicates the status of the removable battery pack when the removable battery pack is not connected to the defibrillation circuitry, and
    wherein the defibrillation indicator indicates the status of the defibrillation circuitry and the removable battery pack when the removable battery pack is connected to the defibrillation circuitry, and wherein the automated external defibrillator comprises a battery well constructed and arranged to house the removable battery pack.

4. The automated external defibrillator of claim 3, wherein the visual output is a light.

* * * * *